(12) United States Patent
Verma et al.

(10) Patent No.: US 11,000,300 B2
(45) Date of Patent: May 11, 2021

(54) MAGNETICALLY COUPLED VASCULAR SNARE SYSTEM AND METHOD

(71) Applicant: Atrial Systems, LLC, Pensacola, FL (US)

(72) Inventors: Sumit Verma, Pensacola, FL (US); Sahil Verma, Pensacola, FL (US)

(73) Assignee: Atrial Systems, LLC, Pensacola, FL (US)

( * ) Notice: Subject to any disclaimer, the term of this patent is extended or adjusted under 35 U.S.C. 154(b) by 182 days.

(21) Appl. No.: 16/390,133

(22) Filed: Apr. 22, 2019

(65) Prior Publication Data
US 2020/0330112 A1 Oct. 22, 2020

(51) Int. Cl.
| | | |
|---|---|---|
| *A61B 17/221* | (2006.01) | |
| *A61B 17/3205* | (2006.01) | |
| *A61M 25/01* | (2006.01) | |
| *A61B 17/22* | (2006.01) | |
| *A61N 1/05* | (2006.01) | |

(52) U.S. Cl.
CPC ...... *A61B 17/221* (2013.01); *A61B 17/32056* (2013.01); *A61M 25/0127* (2013.01); *A61B 2017/22035* (2013.01); *A61N 2001/0578* (2013.01)

(58) Field of Classification Search
CPC .......... A61B 17/221; A61B 17/32056; A61B 2017/22035; A61B 2017/2212; A61B 2017/2217; A61F 2002/9528; A61F 2002/9534; A61N 2001/0578
See application file for complete search history.

(56) References Cited

U.S. PATENT DOCUMENTS

| | | | | |
|---|---|---|---|---|
| 5,624,430 | A | * | 4/1997 | Eton ................. A61M 25/0127 606/1 |
| 5,697,936 | A | | 12/1997 | Shipko |
| 6,379,319 | B1 | * | 4/2002 | Garibotto ............... A61B 17/11 600/585 |
| 7,316,655 | B2 | | 1/2008 | Garibotto |
| 7,402,151 | B2 | | 7/2008 | Rosenman |
| 7,785,250 | B2 | | 8/2010 | Nakao |
| 8,192,430 | B2 | * | 6/2012 | Goode ............... A61B 18/1492 606/45 |
| 9,220,523 | B2 | * | 12/2015 | Taylor ................ A61B 17/3468 |
| 10,071,231 | B2 | * | 9/2018 | Yokota ............ A61M 25/09041 |
| 10,736,632 | B2 | * | 8/2020 | Khairkhahan . A61B 17/320016 |
| 2004/0225233 | A1 | | 11/2004 | Frankowski |
| 2005/0209609 | A1 | * | 9/2005 | Wallace ................. A61B 17/50 606/113 |

(Continued)

*Primary Examiner* — Ryan J. Severson
(74) *Attorney, Agent, or Firm* — AdamsIP, LLC; Stephen Thompson; James Hunter Adams

(57) ABSTRACT

A vascular snare system and method for extracting elongated objects such as pacemaker pacing leads or defibrillator leads from the vasculature of a patient are provided. The system utilizes a sheath having a lumen through which two wire elements are deployed to snare and extract a lead. Each wire element has a magnet disposed at its distal end. The wire elements may be manipulated to form a closed loop transversely around a midsection or central portion of the body of the lead by coupling the magnets to each other. The wire elements may then be utilized to extract the lead from the vasculature of the patient through the lumen.

18 Claims, 7 Drawing Sheets

(56) References Cited

U.S. PATENT DOCUMENTS

| | | | |
|---|---|---|---|
| 2005/0228422 A1* | 10/2005 | Machold | A61B 17/00234 |
| | | | 606/167 |
| 2008/0188850 A1* | 8/2008 | Mody | A61B 18/1492 |
| | | | 606/41 |
| 2010/0286791 A1 | 11/2010 | Goldsmith | |
| 2011/0098720 A1 | 4/2011 | Taylor | |
| 2014/0277087 A1* | 9/2014 | Manning | A61F 2/01 |
| | | | 606/200 |
| 2016/0235422 A1* | 8/2016 | Al-Jilaihawi | A61B 17/221 |
| 2017/0232237 A1* | 8/2017 | Yokota | A61B 17/22031 |
| | | | 604/264 |
| 2018/0008268 A1* | 1/2018 | Khairkhahan | A61B 17/3205 |
| 2020/0138535 A1* | 5/2020 | Adams | A61B 17/22031 |
| 2020/0330112 A1* | 10/2020 | Verma | A61B 17/32056 |

\* cited by examiner

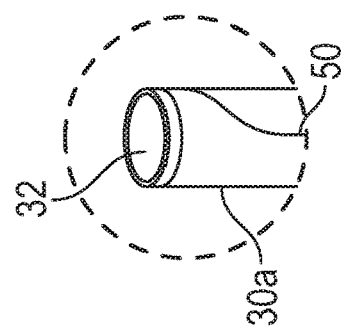
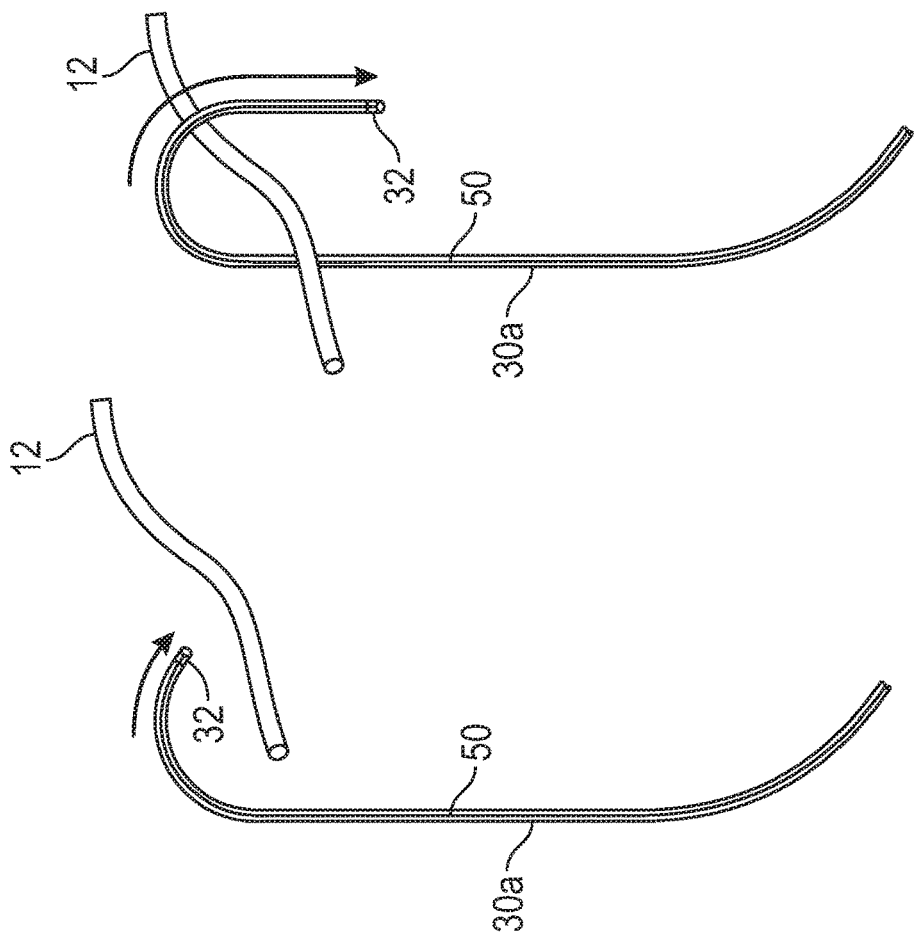

MAGNETICALLY COUPLED VASCULAR SNARE SYSTEM AND METHOD

FIELD OF THE DISCLOSURE

The subject matter of the present disclosure refers generally to systems and methods for extracting elongated objects from the vasculature of a patient.

BACKGROUND

Vascular snares are endovascular devices that are used to extract foreign objects from the vasculature of patients. Such foreign objects may include inferior vena cava filters, stents, intracardiac pacing and defibrillator leads. Vascular snares typically comprise one or more radiopaque loops of wire housed inside a catheter or similar sheath structure. The loops of wire may be forced out from the catheter to engage the foreign object to be extracted and then retracted back into the catheter to extract the object. Examples of such snares include single-loop snares, such as a goose neck snare, and multi-loop snares that have a plurality of individual loops in order to increase the probability of capture of the foreign object. These snare systems have closed loops that may be used to extract inferior vena cava filters by engaging a hook on the filter. Such snare systems may also be used to extract pacing leads or defibrillator leads when the lead has a free end that one or more loops of the snare can be positioned around before retracting the loop back into the snare catheter. A lead may have a free end if the lead breaks, is pulled out of a header, or is abandoned in the vasculature. However, when a free end of a lead is not available for looping the snare around the end of the lead, such closed loop snare systems are ineffective in extracting leads.

Some snare systems have two interlocking closed loops that may be utilized to engage a midsection or central portion of a continuous, elongated lead. Such a snare system may have a first hook-shaped loop with a wide opening and a second loop with a narrow opening. The first loop may be hooked around a central portion of the lead and the second loop may be inserted through the opening in the first loop between the lead and the hooked end of the first loop. When the two loops are retracted, the loops then snare the central portion of the lead for extraction. However, there are deficiencies with this type of snare. When traction is applied to the body of the lead, the hooked loop may straighten, thereby causing inadvertent release of the lead, in which case the procedure must be repeated. In addition, proper placement of the two loops in relation to the lead may be difficult in two dimensions during fluoroscopy when using this type of snare.

There are a number of other limitations with currently known snares, particularly when applied to the extraction of elongated objects such as pacemaker pacing leads and defibrillator leads. For instance, many snares are not steerable so that it is often difficult to engage the lead for extraction, particularly when approaching from a femoral approach. In addition, it is not uncommon for a lead to be inadvertently released when traction is applied to the lead using existing snares because the tensile strength of the lead often exceeds the capability of the snare to maintain a hold on the lead. If the lead is inadvertently released from the snare, the entire snaring procedure must be repeated. Procedural times may be long when trying to snare an elongated pacing or defibrillator lead. This not only adds risk to the patient by increasing anesthesia time, but also increases physician and patient exposure to X-ray, which may lead to radiation burns as well as long-term health effects such as cancer. In addition, once a lead is secured by the snare, extraction often requires an assistant to apply force in order to keep the lead ensnared to prevent inadvertent release and to apply traction to the lead to free the lead and remove it from the vasculature. Thus, a well-trained assistant is typically required. Furthermore, existing snares are often bulky and cumbersome to deploy.

Accordingly, a need exists in the art for improved snaring systems and methods that overcome the disadvantages described above, as well as other disadvantages.

SUMMARY

A vascular snare system and a method of using the snare system for extracting elongated objects from the vasculature of a patient are provided. The system may be utilized to extract elongated objects such as pacemaker pacing leads or defibrillator leads. The snare is capable of forming a closed loop around a midsection or central portion of a lead for extracting the lead without the necessity of looping the snare around a free end of the lead. This functioning allows the snare to reliably trap and extract the lead in a manner in which the lead does not become dislodged from the snare or inadvertently released by the snare when traction is applied to the lead.

The system comprises an elongated, flexible sheath having a lumen and two elongated, flexible deployment elements each having a magnet disposed at a distal end of the deployment element. Both of the deployment elements are slidably disposed within the lumen of the sheath. At least one of the deployment elements is preferably at least twice as long as the sheath. The two magnets are configured to couple to each other in a coaxial arrangement.

To use the vascular snare system to extract an elongated lead from the vasculature of a patient, the distal ends of the two deployment elements with magnets secured thereto are sequentially inserted into the lumen at a proximal end of the sheath. A distal end of the sheath is inserted into an access site of a patient, which is preferably a femoral access site but may include other suitable access sites such as a jugular access site. A user then slides the first deployment element axially within the lumen until its distal end exits the lumen at the distal end of the sheath into the patient vasculature. The distal end of the first deployment element is then positioned on an opposite side of a midsection of the elongated lead to be extracted. Next, the user slides the second deployment element axially within the lumen until its distal end exits the lumen at the distal end of the sheath.

Once the magnets disposed at the distal end of each deployment element are deployed from the lumen, a loop is formed transversely around the elongated body of the lead by positioning the first and second magnets adjacent to each other to cause the magnets to couple to each other. The magnets are configured to couple together in a coaxial arrangement with each other and with the deployment elements. Once the magnets are coupled to form a closed loop around a midsection or central portion of the lead, the user slides both the first and second deployment elements simultaneously in opposite axial directions within the lumen to move the magnets coupled to each other until the coupled magnets exit the lumen at the proximal end of the sheath exterior to the patient. Thus, when the magnets are removed from the patient, only one of the deployment elements is disposed within the lumen and looped around the body of the lead. This deployment element may then be retracted through the lumen by simultaneously pulling opposing ends of the element in a direction away from the distal end of the sheath. As this deployment element is retracted from the lumen while being looped around the lead, the lead is also extracted from the vasculature of the patient through the lumen. Thus, the present snare system may be utilized to form a completely closed loop around a central portion of the lead, which eliminates the possibility of the snare releasing the lead due to insufficient force applied by the snare when traction is applied to the lead.

In a preferred embodiment, the first deployment element has a steerable distal end. The distal end may be bent in order to curve the distal end with the first magnet secured thereto around the body of the lead before coupling the first and second magnets. Steering of the distal end may be controlled by a cable secured to the distal end of the deployment element, which may cause the distal end to bend when traction is applied. This feature may facilitate ease of magnetic coupling to form a closed loop around the body of the lead.

In a preferred embodiment, the second magnet disposed at the distal end of the second deployment element is retractable into a lumen of the second deployment element. This feature allows atraumatic decoupling of the magnets while the device is in use within the patient's vasculature by retracting the second magnet into the second deployment element, thereby causing magnetic decoupling. Decoupling during a lead extraction procedure may be advantageous if entrapment of cardiac tissue occurs at the time of magnetic coupling to form the loop around the lead to be extracted. By providing for atraumatic decoupling while the device is in use, the operator of the device may decouple the magnets and then maneuver the deployment elements to re-couple the magnets for lead extraction without causing further damage to cardiac tissue.

The foregoing summary has outlined some features of the system and method of the present disclosure so that those skilled in the pertinent art may better understand the detailed description that follows. Additional features that form the subject of the claims will be described hereinafter. Those skilled in the pertinent art should appreciate that they can readily utilize these features for designing or modifying other structures for carrying out the same purpose of the system and method disclosed herein. Those skilled in the pertinent art should also realize that such equivalent designs or modifications do not depart from the scope of the system and method of the present disclosure.

DESCRIPTION OF THE DRAWINGS

These and other features, aspects, and advantages of the present disclosure will become better understood with regard to the following description, appended claims, and accompanying drawings where:

FIG. 5A shows a perspective view of a component of a vascular snare system in accordance with the present disclosure.

FIG. 5B shows a perspective view of a component of a vascular snare system in accordance with the present disclosure.

FIG. 5C shows a perspective view of a component of a vascular snare system in accordance with the present disclosure.

FIG. 5D shows a partial view of a component of the vascular snare system shown in FIG. 5A in accordance with the present disclosure.

DETAILED DESCRIPTION

In the Summary above and in this Detailed Description, and the claims below, and in the accompanying drawings, reference is made to particular features, including method steps, of the invention. It is to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with/or in the context of other particular aspects of the embodiments of the invention, and in the invention generally.

The term "comprises" and grammatical equivalents thereof are used herein to mean that other components, steps, etc. are optionally present. For example, a system "comprising" components A, B, and C can contain only components A, B, and C, or can contain not only components A, B, and C, but also one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

Figure 1:
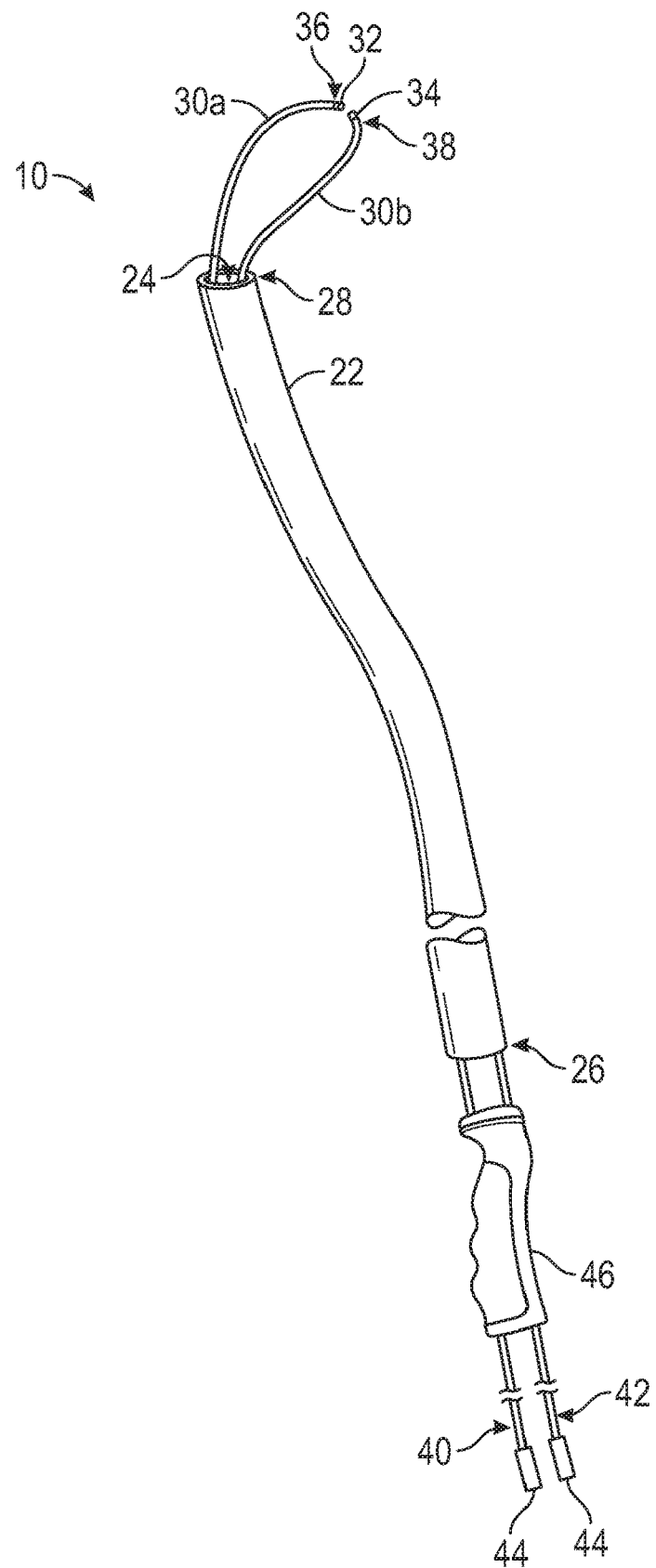
FIG. 1 shows a perspective view of a vascular snare system in accordance with the present disclosure.
Figure 2:
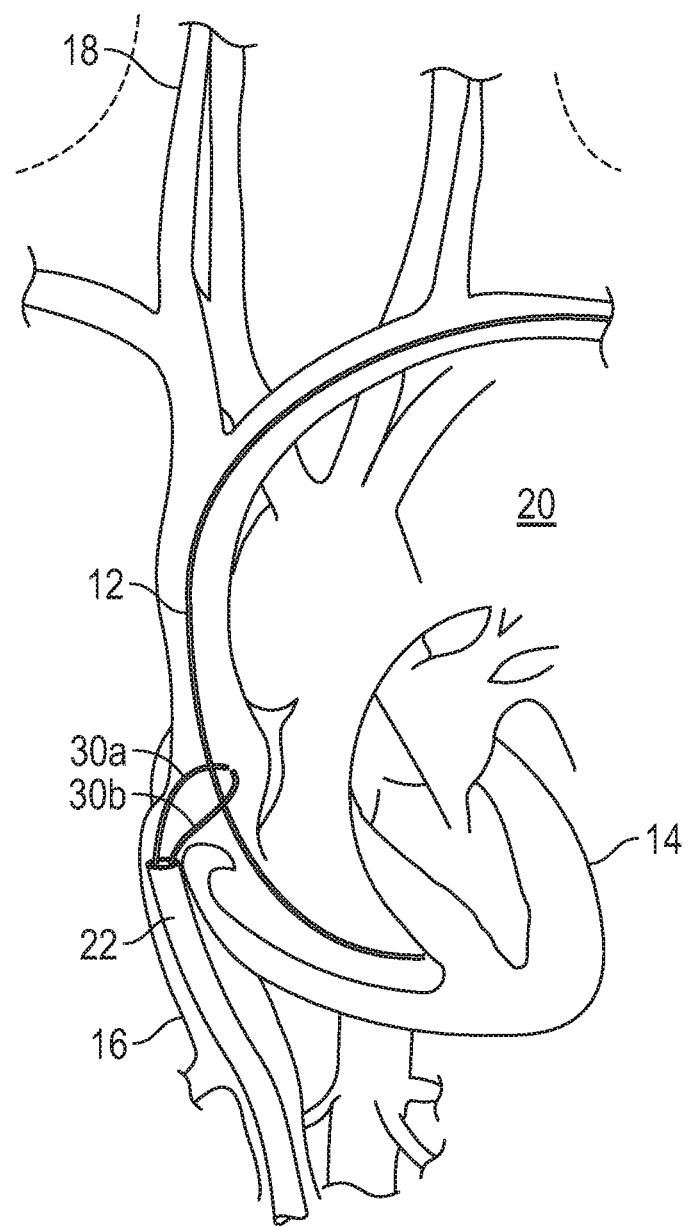
FIG. 2 shows a partial perspective view of a vascular snare system in use in accordance with the present disclosure.
Figures 3, 3A:
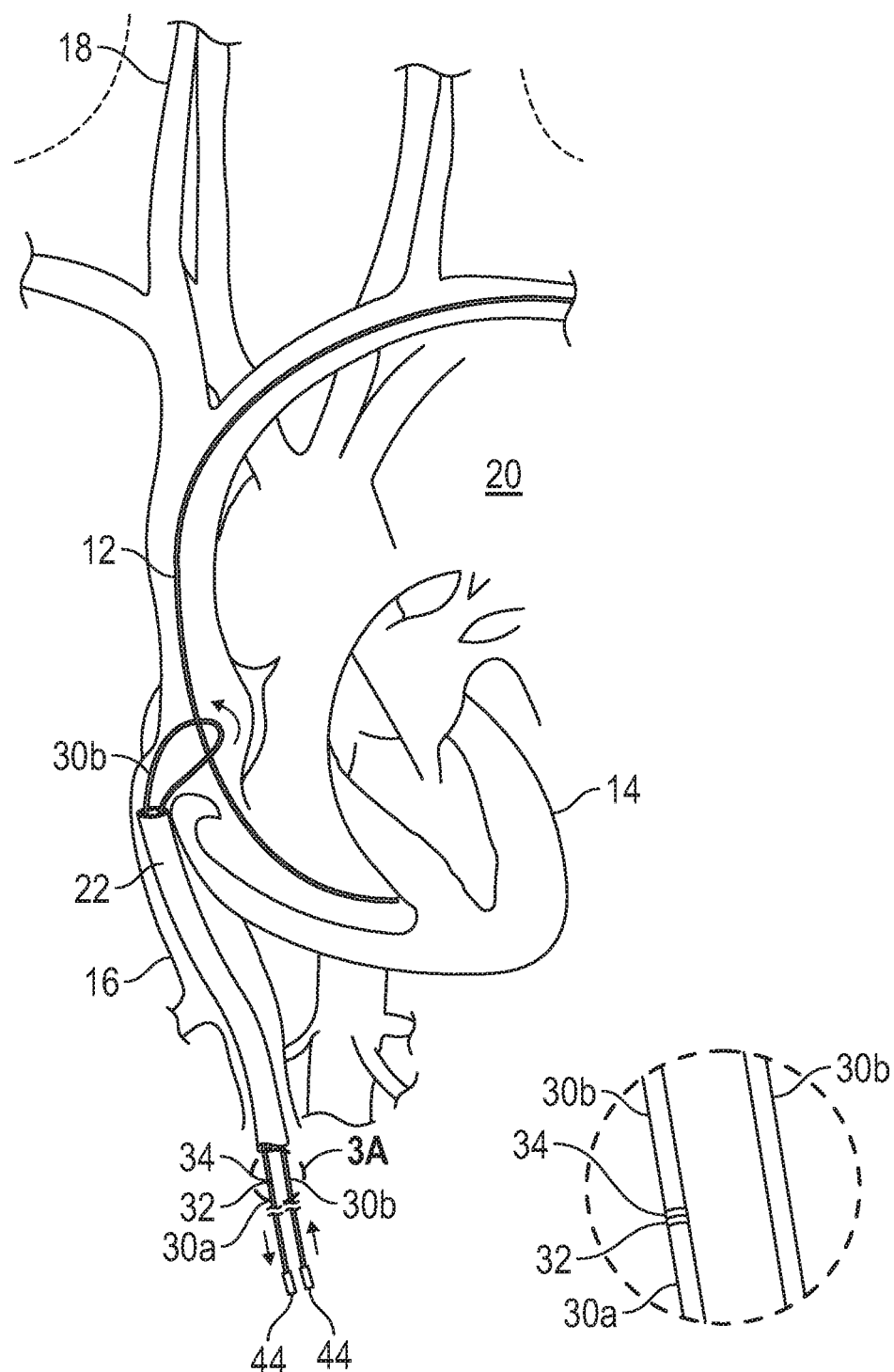
FIG. 3 shows a perspective view of a vascular snare system in use in accordance with the present disclosure.
FIG. 3A shows a partial view of the vascular snare system shown in FIG. 3 in accordance with the present disclosure
Figure 4:
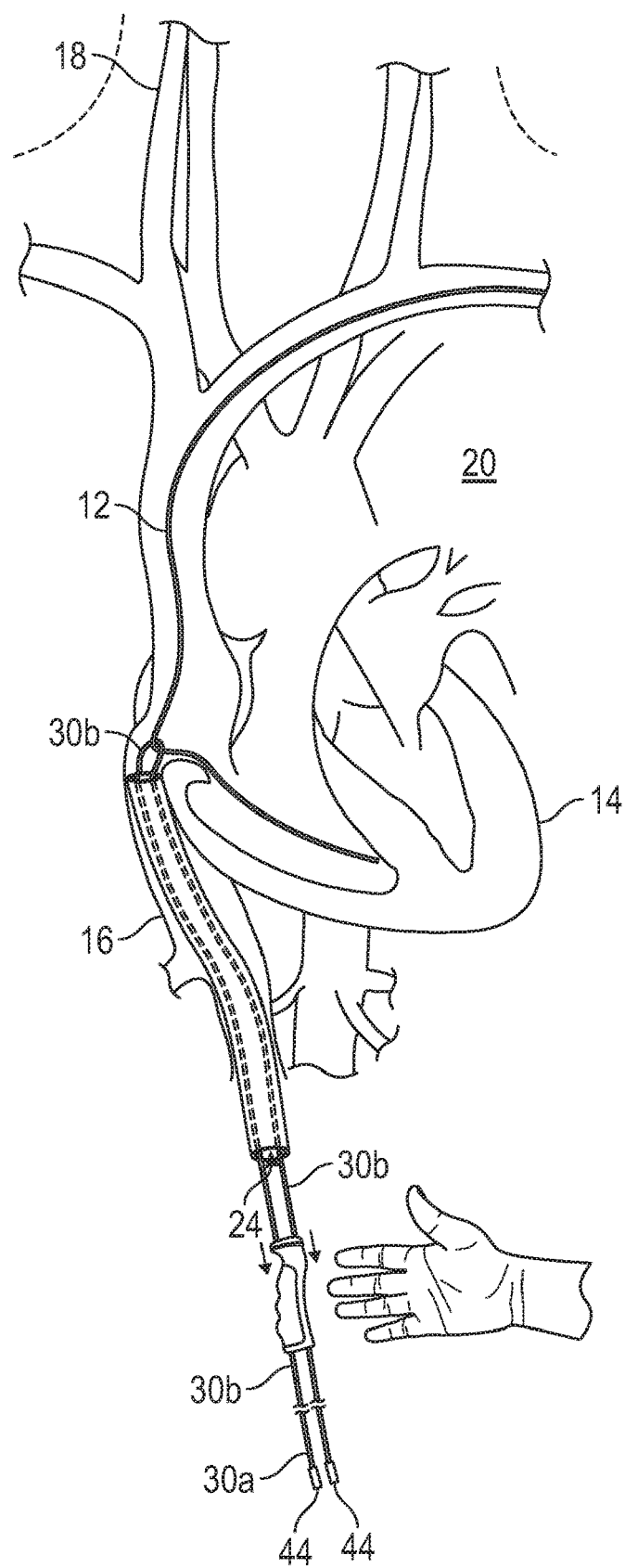
FIG. 4 shows a perspective view of a vascular snare system in use in accordance with the present disclosure.

A vascular snare system 10 and a method of using the snare system 10 for extracting elongated objects 12 from the vasculature of a patient 20 are provided. FIGS. 1-7 illustrate preferred embodiments of the system 10. FIGS. 2-4 show the system 10 in use on a patient 20 for the extraction of a pacing lead 12 from the heart 14 of the patient 20. The system 10 may be utilized to extract any elongated object 12 from the vasculature of a patient, including, but not limited to, a pacemaker pacing lead or a defibrillator lead. The system 10 may also be used to extract any other type of foreign object, such as an inferior vena cava filter, having a hook or similar element that can be snared by a loop. The system 10 accesses the patient's vasculature via an access site. In a preferred embodiment, as best seen in FIG. 2, the system 10 is used to extract a lead 12 via the inferior vena cava 16, which is preferably accessed through a femoral approach. The system 10 may optionally be used to access the vasculature via a patient's right internal jugular 18 or any other suitable access site. As best seen in FIG. 3, the snare system 10 is capable of forming a closed loop around a continuous length of a midsection or central portion of a lead 12 for extracting the lead 12 without the necessity of looping a snare around a free end of the lead 12. This functioning allows the snare to reliably trap and extract the lead 12 in a manner in which the lead does not become dislodged from or inadvertently released by the snare when traction is applied to the lead 12.

The snare system 10 comprises an elongated, flexible sheath 22 having a lumen 24. The sheath 22 has a proximal end 26 and a distal end 28. The system 10 further comprises a first elongated, flexible deployment element 30a having a first magnet 32 disposed at a distal end 36 of the first deployment element 30a and a second elongated, flexible deployment element 30b having a second magnet 34 disposed at a distal end 38 of the second deployment element 30b. Both of the deployment elements 30 are slidably disposed within the lumen 24 of the sheath 22 so that the distal end 36, 38 of each of the deployment elements 30 can be inserted into the lumen 24 and both elements 30 can be moved back and forth in an axial direction within the lumen. In a preferred embodiment, at least one of the deployment elements 30 is at least twice as long as the sheath 22. The first magnet 32 and the second magnet 34 are configured to couple to each other in a coaxial arrangement, as best seen in FIG. 3A.

To use the vascular snare system 10 to extract an elongated lead 12 from the vasculature of a patient 20, a user sequentially inserts the distal end 36 of the first deployment element 30a with magnet 32 and the distal end 38 of the second deployment element 30b with magnet 34 into the lumen 24 at the proximal end 26 of the sheath 22. When sequentially inserting the first and second deployment elements 30a and 30b into the lumen 24, a distance should be maintained between the first magnet 32 and the second magnet 34 that is sufficient to avoid magnetic coupling within the lumen 24 before deploying the elements 30 outside the lumen. The distal end 28 of the sheath 22 is inserted into an access site of the patient 20 and moved to within close proximity to the lead 12 within the vasculature, as shown in FIG. 2. Alternatively, the sheath 22 may be inserted into the vasculature before inserting the deployment elements 30 into the lumen 24. The user then slides the first deployment element 30a axially within the lumen 24 until the distal end 36 exits the lumen 24 at the distal end 28 of the sheath 22 into the patient vasculature. The distal end 36 of the first deployment element 30a is then positioned on an opposite side of the elongated lead 12 to be extracted, as best seen in FIG. 2, so that a loop may be formed around the body of the lead 12. Next, the user slides the second deployment element 30b axially within the lumen 24 until the distal end 38 exits the lumen 24 at the distal end 28 of the sheath 22.

Figure 6A:
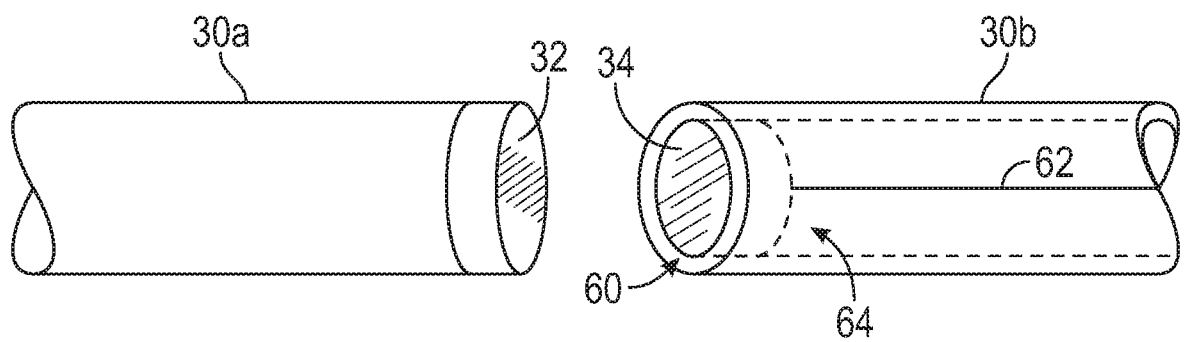
FIG. 6A shows a partial view of components of a vascular snare system in accordance with the present disclosure.

Once the magnets 32, 34 disposed at the distal end of each respective deployment element 30 are deployed from the lumen 24, the user manipulates the deployment elements 30a and 30b to form a loop transversely around the elongated body of the lead 12, as shown in FIG. 2. The loop is formed by positioning the first magnet 32 and the second magnet 34 adjacent to each other to cause the magnets to couple to each other, thereby completing the closed loop around the body of the lead 12. The magnets 32, 34 are configured to couple together in a coaxial arrangement with each other and with the deployment elements 30, as best seen in FIG. 3A. As used herein, the coaxial arrangement is based on an axis of each of the elongated deployment elements 30. FIG. 6A additionally illustrates the magnets 32, 34 in a coaxial arrangement with each other and with deployment elements 30a and 30b as the magnets approach each other just prior to magnetic coupling.

As shown in the figures, the magnets 32, 34 generally have the shape of a flat disc. Alternatively, the magnets 32, 34 may have other suitable shapes configured to facilitate ease of coupling in a desired orientation. In one embodiment, the first 32 and second magnets 34 may have compatible shapes that fit together when coupled. For instance, in one alternative embodiment, the first magnet 32 may have a ball shape or a disc shape, and the second magnet 34 may have a socket sized and shaped to receive the ball or the disc of the first magnet. The first magnet 32 may alternatively have a cone shape, and the second magnet 34 may have a compatible socket. Such compatible shapes may aid in keeping the magnets 32, 34 coupled to each other in a coaxial arrangement and minimize the possibility of unwanted non-coaxial coupling, which may not provide the strongest coupling and may expand the overall diameter of coupled magnets. Compatible shapes may also facilitate coaxial coupling even if the magnets 32, 34 approach each other at an angle during coupling. The magnets 32, 34 may be secured to the distal ends 36, 38 of each respective deployment elements 30a, 30b in any suitable manner, such as with an adhesive or by soldering, or may be supported at the distal end of each deployment element by other suitable means.

In addition, the magnets 32, 34 and both deployment elements 30 preferably have substantially equal diameters, as best seen in FIG. 3A, to facilitate smooth axial movement of the elements 30 and coupled magnets 32, 34 within the lumen 24 while minimizing the potential for the coupled magnets to become snagged during the extraction procedure.

Once the magnets 32, 34 are coupled to form a closed loop around a midsection or central portion of the lead 12, the user then slides both the first and second deployment elements 30 simultaneously in opposite axial directions within the lumen 24 as indicated by the arrows shown in FIG. 3. This action moves the magnets 32, 34 coupled to each other axially within the lumen 24 until the coupled magnets exit the lumen 24 at the proximal end 26 of the sheath 22 exterior to the patient 20, as shown in FIG. 3. Thus, when the magnets 32, 34 are removed from the patient 20, only one of the deployment elements 30 is disposed within the lumen 24 and looped around the body of the lead 12. Removal of the magnets 32, 34 from the sheath 22 allows only one of the deployment elements 30 to be used for lead 12 extraction, thereby eliminating the possibility of the magnets decoupling when traction is applied to the lead 12 for extraction. As shown in FIG. 3, the deployment elements 30 are fed in a counterclockwise direction so that only the second deployment element 30b remains in the sheath 22, though the deployment elements 30 may alternatively be fed in a clockwise direction so that the first deployment element 30a remains in the sheath 22. Because only one deployment element 30 is used to form the loop at the distal end 28 of the sheath 22 with opposing ends of the deployment element 30 extending outward from the lumen 24 at the proximal end 26 of the sheath 22, this single deployment element 30 utilized for forming the loop should be at least twice as long as the sheath 22, though this element 30 is preferably long enough to allow an operator to grip ends of the element 30 outside the proximal end 26 of the sheath 22 for lead extraction, as shown in FIG. 4. The length of the sheath 22 and the deployment elements 30 should be sized according to the particular extraction procedure being performed.

The deployment element 30b used to form the loop may then be retracted through the lumen 24 by simultaneously pulling opposing ends of the element 30b in a direction away from the distal end 28 of the sheath 22, as indicated by the arrows shown in FIG. 4. This action causes the deployment element 30b to tighten around the lead 12 and draw the lead 12 into the sheath 22. As deployment element 30b is retracted from the lumen 24, the lead 12 is thus extracted from the vasculature of the patient 20 through the lumen 24. Thus, the present snare system 10 may be utilized to form a completely closed loop around a central portion of the lead 12, which eliminates the possibility of the snare loop releasing the lead 12 due to insufficient force applied by the snare to the body of the lead with when traction is applied to the lead.

In an alternative embodiment, the magnets 32, 34 may be configured to interlock with each other when coupled together. For instance, the magnets 32, 34 may comprise an interlocking screw or ratchet mechanism that removably secures the magnets to each other mechanically in order to supplement the magnetic forces coupling the magnets so that the magnets cannot be inadvertently pulled apart due to tensile forces acting on the deployment elements 30. In this embodiment, the lead 12 may optionally be extracted without removing the coupled, interlocking magnets 32, 34 from the lumen 24 or patient vasculature by simultaneously pulling ends of both elements 30a and 30b.

The sheath 22 may comprise a single sheath structure or optionally an inner telescoping sheath, such as a catheter, for deploying the deployment elements 30 and an outer introducer sheath for introducing the snare system 10 into the patient's vasculature. The deployment elements 30 are preferably constructed of a nonferrous material to prevent interaction with the magnets. In addition, the body of each of the deployment elements 30 preferably has a high degree of tensile strength and flexibility so that the distal ends of the deployment elements may be steered to curve around the lead 12 and so that the elements 30 may be tightened into a tight loop for extraction of the lead 12 without resulting in breakage or fracturing at the site of the loop. The material forming the body of each of the deployment elements 30 may be a braided wire for added tensile strength and flexibility. In a preferred embodiment, the material of construction may be a nonferrous alloy having properties of superelasticity, such as a nickel titanium alloy, also known as Nitinol. Such an alloy may provide a wire 30 having high tensile strength and that may be easily deformed and returned to its original shape. The deployment wires 30 may be pushed, pulled, rotated, or otherwise manipulated as necessary using pull, or torque, handles 44 attached to a proximal end 40 of the first deployment element 30a and to a proximal end 42 of the second deployment element 30b, as shown in FIG. 1. Such manipulation may be performed as necessary to position the magnets 32, 34 adjacent to each other for coupling and to slide the deployment elements 30 back and forth within the lumen 24.

In a preferred embodiment, as shown in FIG. 1, the snare system 10 further comprises a flexible gripping tube 46 arranged around at least one of the first and second deployment elements 30 and positioned at the proximal end 26 of the sheath 22. The gripping tube 46 may be squeezed by the user to grip one or both of the deployment elements 30 to manipulate the elements during the extraction procedure or to apply traction to the lead 12 by pulling on one or both deployment elements 30 to extract the lead. As shown in FIG. 4, the coupled magnets 32, 34 may be fed through the gripping tube 46 so that the gripping tube 46 is positioned around only one of the deployment elements 30b so that a single deployment element 30b may be gripped to apply traction to the lead 12 for lead extraction through the lumen 24.

In a preferred embodiment, as shown in FIG. 5, the first deployment element 30a has a steerable distal end 36. The distal end 36 of the element 30a may be bent in order to curve the distal end 36 with the first magnet 32 disposed thereon around the body of the lead 12 before coupling the first and second magnets 32, 34. In this embodiment, the bending or curving of the distal end 36 may facilitate the positioning of the distal end 36 of the first deployment element 30a on an opposite side of the lead 12 to be extracted by curving the distal end 36 around the body of the lead 12, as shown in FIGS. 5B and 5C. In a preferred embodiment, the distal end 36 may be curved radially up to 270 degrees. The bending or curving of the distal end 36 of the first deployment element 30a may facilitate the coupling of the magnets 32, 34 by positioning the magnets in a coaxial orientation relative to each other prior to coupling. As shown in FIGS. 5A-5D, steering of the distal end 36 may be controlled by a steering tendon or cable 50 secured to the distal end 36 of the first deployment element 30a. As best seen in FIG. 5D, the cable 50 may be housed within a lumen of deployment element 30a, or, alternatively, interlocking with a braided wire element 30a. The cable 50 may cause the distal end 36 of the wire element 30a to bend or curve when traction is applied to the cable 50, with the degree of curvature determined by the amount of traction applied, as shown in FIGS. 5B and 5C. As shown in FIG. 5D, the cable 50 may be secured to the deployment element 30a internally on one side of the lumen in the deployment element near the base of the magnet 32. The cable 50 may be secured in any suitable manner, such as soldering the cable to the element. Thus, when traction is applied to the cable 50 secured on one side of the element, the traction causes the deployment element 30a to curve in a direction toward the attachment point, thereby allowing the distal end of the element to be steered in a controlled manner. Alternatively, any steering mechanism suitable for steering and manipulating the distal end of an elongated snare wire may be utilized to facilitate ease of magnetic coupling to form a closed loop around a central portion of the body of an elongated lead 12.

Figure 6B:
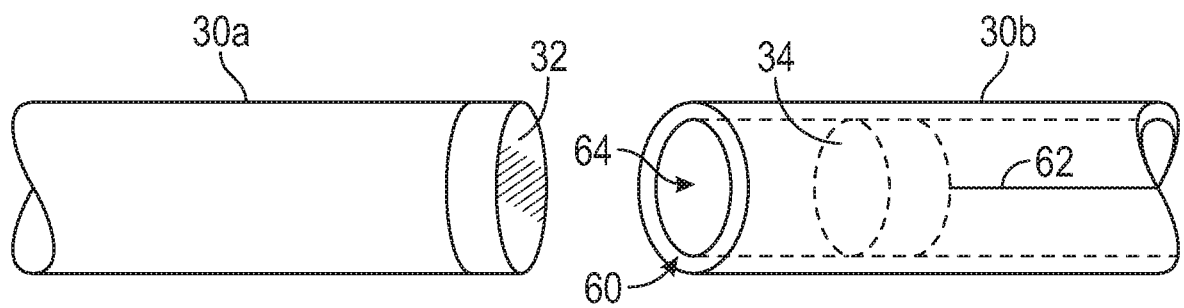
FIG. 6B shows a partial view of components of a vascular snare system in accordance with the present disclosure.

In a preferred embodiment, as shown in FIG. 6, the second magnet 34 disposed at the distal end 38 of the second deployment element 30b is retractable into a lumen 64 within the second deployment element 30b. This feature allows atraumatic decoupling of the magnets while the device is in use within the patient's vasculature by retracting the second magnet 34 into the second deployment element 30b, as shown in FIG. 6B, thereby causing decoupling of the magnets 32, 34. To facilitate retraction of the magnet 34, the second deployment element 30b may have a cable 62 that is secured to the second magnet 34 and that extends through the lumen 64 of the second deployment element 30b to the proximal end 42 of the second deployment element 30b. The cable 62 has sufficient rigidity to withdraw the magnet 34 by pulling the cable 62 and to reposition the magnet 34 at the distal end 38 of the second deployment element 30b by pushing the cable 62. The cable 62 may be soldered to the magnet 34 in a centered position on the magnet or may be secured thereto in any other suitable manner.

In this embodiment, the second magnet 34 preferably has a smaller diameter than the first magnet 32, and the distal end 38 of the second deployment element 30b has an annular edge 60 around an opening of the lumen 64 within the second deployment element 30b, as shown in FIG. 6. The annular edge 60 has an internal diameter that is smaller than the diameter of the first magnet 32 so that the edge prevents the first magnet 32 from being drawn into the second deployment element 30b when the second magnet 34 is retracted. The annular edge 60 may be defined by the thickness of the walls of the second deployment element 30b, or may alternatively be formed by an annular lip or ring disposed at the distal end 38 of the second deployment element 30b.

FIG. 6A illustrates the magnets 32 and 34 approaching each other in an axial arrangement for magnetic coupling in order to form the loop around the lead 12 to be extracted. The first magnet 32 is secured to the distal end 36 of the first deployment element 30a and preferably has the same diameter as the first deployment element 30a. The first magnet 32 preferably also has the same diameter as the second deployment element 30b, but a larger diameter than the second magnet 34. After magnetic coupling, the magnets 32 and 34 may be decoupled with the device 10 in use by retracting the second magnet 34 using the cable 62, as shown in FIG. 6B. When the second magnet 34 is retracted while being coupled to the first magnet 32, the annular edge 60 contacts the face of the first magnet 32 and prevents the first magnet 32 from being retracted into the lumen 64 of the second deployment element 30b with the second magnet 34, thereby causing decoupling of the magnets.

Decoupling of the magnets 32, 34 during a lead 12 extraction procedure may be advantageous if entrapment of cardiac tissues, such as valve leaflets, papillary muscles, chordal structures, or the atrial or ventricular wall, occurs at the time that the magnets 32, 34 are coupled together to form the loop around the lead to be extracted. In this case, the magnets need to be decoupled to prevent damage to the cardiac tissue. Thus, decoupling the magnets 32, 34 is an optional step in the extraction procedure only when atraumatic decoupling is required. Retraction of one of the magnets provides for atraumatic decoupling while the device 10 is in use, which allows the operator of the device to first decouple the magnets 32, 34 and then maneuver the deployment elements 30a and 30b to re-couple the magnets for lead extraction without causing further damage to cardiac tissue.

Figure 7:
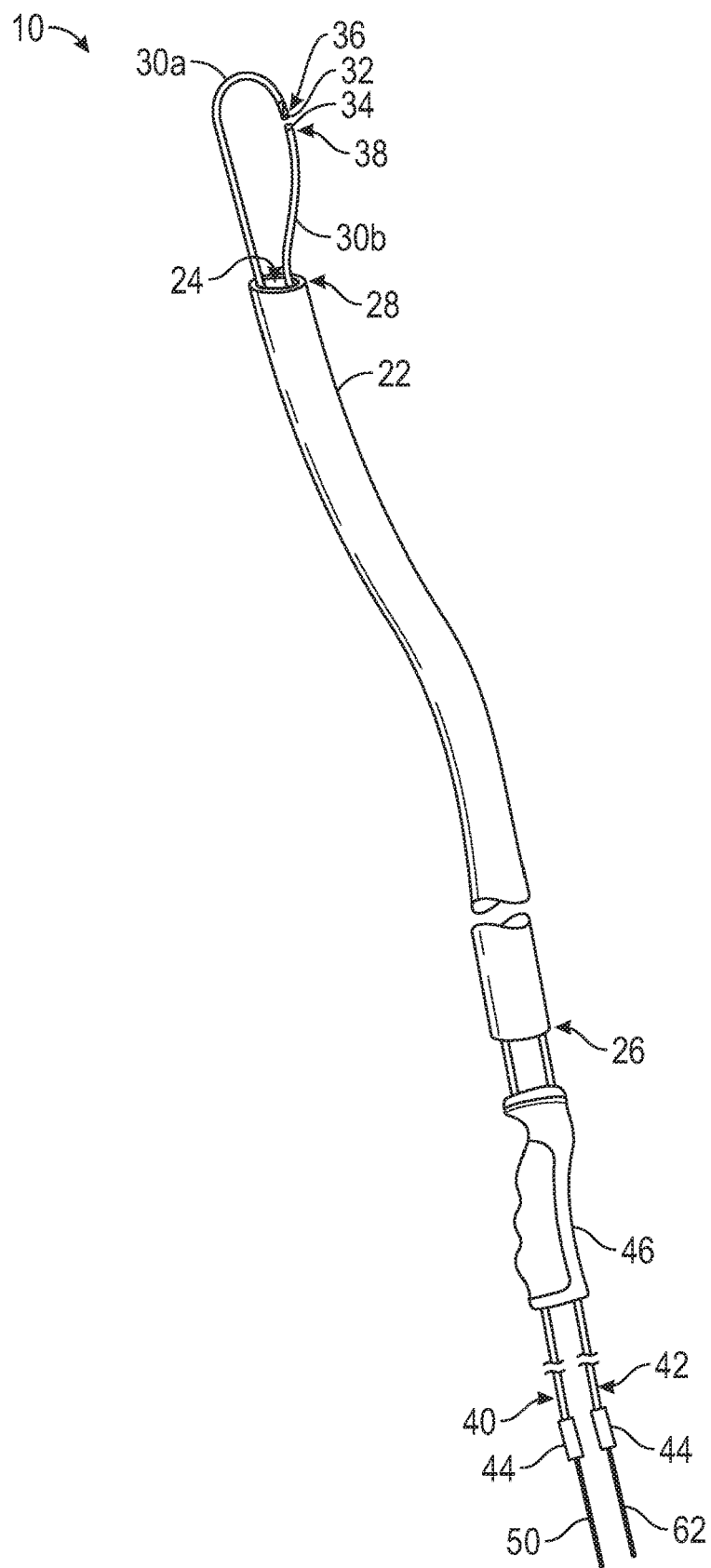
FIG. 7 shows a perspective view of a vascular snare system in accordance with the present disclosure.

In a preferred embodiment, as shown in FIG. 7, the first deployment element 30a has a steerable distal end 36, as shown in FIG. 5, and the second deployment element 30b has a retractable magnet 34, as shown in FIG. 6. This configuration may allow the operator of the device 10 to steer the distal end 36 of the first deployment element 30a around the lead 12 to be extracted for ease of magnetic coupling, while also giving the operator the ability to decouple the magnets 32, 34 during the procedure, if necessary. In this embodiment, as shown in FIG. 7, the handles 44 may have openings at the proximal end 42 of the deployment elements 30 to allow access to and control of cables 50 and 62 extending through elements 30a and 30b, respectively, for steering the first deployment element 30a and for retracting the second magnet 34, respectively. The cables 50 and 62 allow the operator to perform these steps from the proximal end 26 of the sheath 22 external to the body of the patient 20. In an alternative embodiment, both of the deployment elements 30a and 30b may have steerable distal ends and/or retractable magnets.

It is understood that versions of the present disclosure may come in different forms and embodiments. Additionally, it is understood that one of skill in the art would appreciate these various forms and embodiments as falling within the scope of the invention as disclosed herein.

What is claimed is:

1. A vascular snare system for extracting objects in the vasculature of a patient, said vascular snare system comprising:
    a flexible sheath having a first lumen,
    a first flexible deployment element having a first magnet disposed at a distal end of the first deployment element, and
    a second flexible deployment element having a second magnet disposed at a distal end of the second deployment element,
    wherein the first and second deployment elements are both slidably disposed within the first lumen,
    wherein the second deployment element has a second lumen within the second deployment element, wherein the second magnet is retractable into the second lumen of the second deployment element, and wherein the first magnet is not retractable into the second lumen of the second deployment element,
    wherein at least one of the first and second deployment elements has a steerable distal end, and
    wherein the first and second magnets are configured to couple to each other in a coaxial arrangement.

2. The vascular snare system of claim 1, wherein at least one of the first and second deployment elements is at least twice as long as the sheath.

3. The vascular snare system of claim 1, wherein the second magnet has a smaller diameter than the first magnet, wherein the distal end of the second deployment element has an annular edge around an opening of the second lumen within the second deployment element, wherein the annular edge has an internal diameter that is smaller than the diameter of the first magnet, wherein a cable is secured to the second magnet, and wherein the cable extends through the second lumen within the second deployment element to a proximal end of the second deployment element.

4. The vascular snare system of claim 1, wherein the first deployment element has a steerable distal end.

5. The vascular snare system of claim 4, wherein the second magnet has a smaller diameter than the first magnet, wherein the distal end of the second deployment element has an annular edge around an opening of the second lumen within the second deployment element, wherein the annular edge has an internal diameter that is smaller than the diameter of the first magnet, wherein a cable is secured to the second magnet, and wherein the cable extends through the second lumen within the second deployment element to a proximal end of the second deployment element.

6. The vascular snare system of claim 1, wherein the first and second magnets and the first and second deployment elements each have an equal diameter.

7. The vascular snare system of claim 1, wherein the first and second deployment elements are both made of a non-ferrous material.

8. The vascular snare system of claim 1, wherein the system further comprises a flexible gripping tube arranged around at least one of the first and second deployment elements and positioned at a proximal end of the sheath.

9. A method of extracting an elongated object from the vasculature of a patient, said method comprising the steps of:
    providing a vascular snare system comprising:
        a flexible sheath having a lumen,
        a first flexible deployment element having a first magnet disposed at a distal end of the first deployment element, and
        a second flexible deployment element having a second magnet disposed at a distal end of the second deployment element,
        wherein the first and second deployment elements are both slidably disposed within the lumen, and wherein at least one of the first and second deployment elements is at least twice as long as the sheath, and wherein the first and second magnets are configured to couple to each other in a coaxial arrangement, sequentially inserting the distal end of each deployment element into the lumen at a proximal end of the sheath, inserting a distal end of the sheath into an access site of the vasculature of a patient, sliding the first deployment element until the distal end of the first deployment element exits the lumen at the distal end of the sheath, positioning the distal end of the first deployment element on an opposite side of the elongated object to be extracted, sliding the second deployment element until the distal end of the second deployment element exits the lumen at the distal end of the sheath, forming a loop transversely around the elongated object by positioning the first and second magnets adjacent to each other to cause the magnets to couple to each other in a coaxial arrangement, sliding both the first and the second deployment elements simultaneously in opposite axial directions within the lumen to move the two magnets coupled to each other until the coupled magnets exit the lumen at the proximal end of the sheath exterior to the patient so that only one of the deployment elements is disposed within the lumen and looped around the elongated object, and retracting the one deployment element looped around the object through the lumen by simultaneously pulling opposing ends of the one deployment element in a direction away from the distal end of the sheath, thereby extracting the elongated object from the vasculature through the lumen.

10. The method of claim 9, wherein the first deployment element has a steerable distal end, and wherein the step of positioning the distal end of the first deployment element on an opposite side of the elongated object to be extracted comprises bending the distal end of the first deployment element to curve said distal end around the elongated object to be extracted before the magnets are coupled to each other.

11. The method of claim 10, wherein the second magnet of the second deployment element is retractable into the second deployment element.

12. The method of claim 9, wherein the second magnet of the second deployment element is retractable into the second deployment element.

13. The method of claim 12, wherein the second magnet has a smaller diameter than the first magnet, wherein the distal end of the second deployment element has an annular edge around an opening of a lumen within the second deployment element, wherein the annular edge has an internal diameter that is smaller than the diameter of the first magnet, wherein a cable is secured to the second magnet, and wherein the cable extends through the lumen within the second deployment element to a proximal end of the second deployment element.

14. The method of claim 9, wherein the step of sequentially inserting the distal end of each deployment element into the lumen comprises maintaining a distance between the first and second magnets that is sufficient to avoid magnetic coupling within the lumen.

15. The method of claim 9, wherein the first and second magnets and the first and second deployment elements each have an equal diameter.

16. The method of claim 9, wherein the first and second deployment elements are both made of a nonferrous material.

17. The method of claim 9, wherein the vascular snare system further comprises a flexible gripping tube arranged around opposing ends of the one deployment element looped around the elongated object and positioned at a proximal end of the sheath, wherein the step of retracting the one deployment element comprises gripping the one deployment element with the gripping tube to facilitate retraction.

18. A method of extracting an elongated object from the vasculature of a patient, said method comprising the steps of:

providing a vascular snare system comprising:
a flexible sheath having a lumen,
a first flexible deployment element having a first magnet disposed at a distal end of the first deployment element, and
a second flexible deployment element having a second magnet disposed at a distal end of the second deployment element,
wherein the first and second deployment elements are both slidably disposed within the lumen, and
wherein the first and second magnets are configured to couple to each other in a coaxial arrangement, sequentially inserting the distal end of each deployment element into the lumen at a proximal end of the sheath, inserting a distal end of the sheath into an access site of the vasculature of a patient, sliding the first deployment element until the distal end of the first deployment element exits the lumen at the distal end of the sheath, positioning the distal end of the first deployment element on an opposite side of the elongated object to be extracted, sliding the second deployment element until the distal end of the second deployment element exits the lumen at the distal end of the sheath, forming a loop transversely around the elongated object by positioning the first and second magnets adjacent to each other to cause the magnets to couple to each other in a coaxial arrangement, and retracting the deployment elements through the lumen by simultaneously pulling the deployment elements in a direction away from the distal end of the sheath, thereby extracting the elongated object from the vasculature through the lumen.

* * * * *